US006824980B2

(12) United States Patent
Wang (10) Patent No.: US 6,824,980 B2
(45) Date of Patent: Nov. 30, 2004

(54) ISOMETRIC PRIMER EXTENSION METHOD AND KIT FOR DETECTION AND QUANTIFICATION OF SPECIFIC NUCLEIC ACID

(76) Inventor: Xiao Bing Wang, 1313 York Rd., Suite 201, Lutherville, MD (US) 21093

( * ) Notice: Subject to any disclaimer, the term of this patent is extended or adjusted under 35 U.S.C. 154(b) by 0 days.

(21) Appl. No.: 09/862,417

(22) Filed: May 23, 2001

(65) Prior Publication Data

US 2003/0148525 A1 Aug. 7, 2003

Related U.S. Application Data

(60) Provisional application No. 60/209,987, filed on Jun. 8, 2000, and provisional application No. 60/166,898, filed on Nov. 22, 1999.

(51) Int. Cl.[7] .......................... C12Q 1/68; C12P 19/34; C12M 1/34; C07H 21/02; C07H 21/04
(52) U.S. Cl. .......................... 435/6; 435/7.1; 435/91.1; 435/91.2; 435/287.2; 536/221; 536/23.1; 536/24.3; 536/24.31; 536/24.32; 536/24.33
(58) Field of Search ............................ 435/6, 7.1, 91.1, 435/91.2, 287.2, 91.5, 810; 530/221, 23.1, 24.3, 24.33; 935/6; 536/24.3

(56) References Cited

U.S. PATENT DOCUMENTS

| | | | |
|---|---|---|---|
| 4,948,882 A | * 8/1990 | Ruth | 536/27 |
| 4,965,188 A | 10/1990 | Mullis et al. | |
| 5,521,296 A | * 5/1996 | Okada | 536/25.3 |
| 5,578,467 A | * 11/1996 | Schuster et al. | 435/91.2 |
| 5,650,277 A | 7/1997 | Navot et al. | |
| 5,700,642 A | * 12/1997 | Monforte et al. | 435/6 |
| 5,710,028 A | 1/1998 | Eyal et al. | |
| 5,830,655 A | 11/1998 | Monforte et al. | 435/6 |
| 5,846,710 A | 12/1998 | Bajaj | |
| 5,849,542 A | 12/1998 | Reeve et al. | |
| 5,885,775 A | 3/1999 | Haff et al. | |
| 5,888,778 A | 3/1999 | Shuber | |
| 5,888,819 A | 3/1999 | Goelet et al. | |
| 5,965,363 A | * 10/1999 | Monforte et al. | |
| 5,994,079 A | 11/1999 | De La Rosa et al. | |
| 6,007,987 A | 12/1999 | Cantor et al. | |
| 6,013,431 A | 1/2000 | Söderlund et al. | |
| 6,156,178 A | * 12/2000 | Mansfield et al. | 204/457 |
| 6,221,592 B1 | * 4/2001 | Schwartz | 435/6 |

FOREIGN PATENT DOCUMENTS

| | | |
|---|---|---|
| EP | 0 497 527 A1 | 8/1992 |
| EP | 0 663 447 A2 | 7/1995 |
| RU | 2099426 C1 | 3/1989 |
| RU | 97117182 A | 8/1999 |
| SG | 200103079-0 | 2/2003 |
| WO | WO 96/30545 A1 | 10/1996 |
| WO | WO 99/57318 | 11/1999 |

OTHER PUBLICATIONS

Mizusawa, S. et al., Improvement of the dideoxy chain termination method of DNA sequencing by use of deoxy–7 . . . , vol. 14, (1986), Nucleic Acids Research, pp 1319–1324.*

U.S. patent application Ser. No. 09/618,129, Wang.

Toni R. Prezant and Nathan Fischel–Ghodsian, Trapped–Oligonucleotide Nucleotide Incorporation (TONI) Assay, a Simple Method for Screening Point Mutations, Human Mutation 1:159–164 (1992), pp. 159–164, 1992 Wiley–Liss, Inc.

(List continued on next page.)

Primary Examiner—Jeffrey Siew
(74) Attorney, Agent, or Firm—Charles Vorndran; Thomas, Kayden, Horstemeyer & Risley, LLP (57) ABSTRACT

A method for detecting and/or quantifying a target DNA or RNA present in a sample by a isometric primer extension method is disclosed. The method includes carrying out a primer extension reaction in the absence of a free nucleotide so that the primer extension reaction is stopped where the absent nucleotide would have been inserted. Thus, as the amount of incorporation of a labeled nucleotide on the primer extended product is detected, the amount of the target RNA or DNA in the sample is measured.

38 Claims, 2 Drawing Sheets

---

Target DNA Detection and Quantification (1) Extension with dTTP, dGTP, dCTP, either with ddATP or without dATP (SEQ ID NO:2)
5' TGATCAGCAGGCTGAAATCGTCGTGGATTGCAACGACGCCGACGATTCTCGTCCTTTAAGGCGATAGCAT 3'
3'gtcgtcog————Primer 2————5'   3'cgttgctgoggctgct————5'
                                    (SEQ ID NO:3)   Primer 1

(2) Extension with dATP, dGTP, dCTP, either with ddTTP or without dTTP

5' TGATCAGCAGTGCTGAAATCGTCGTGGATTGCAACGACGCCGACGATTCTCGTCCTTTAAGGCGATAGCAT 3'
3'agcagcacc————Primer 4————5'   3'aagagcaggaaa————5'
                                    (SEQ ID NO:4)   Primer 3

(3) Extension with dATP, dGTP, dTTP, either with ddCTP or without dCTP

5' TGATCAGCAGTGCTGAAATCGTCGTGGATTGCAACGACGCCGACGATTCTCGTCCTTTAAGGCGATAGCAT 3'
3'tttag————Primer 6————5'   3'agtaaatt————Primer 5————5'

Line represents primer sequence. Small letters a, g, c, and t are bases extended from the primer, some of which are labeled with a detectable marker. u and t are used interchangeably.

OTHER PUBLICATIONS

Nishisho et al., Mutations of Chromosome 5q21 Genes in FAP and Colorectal Cancer Patients. SCIENCE 253, 665–669 (1991).

Konopka et al., An Alteration of the Human c–abl Protein in K562 Leukemia Cells Unmasks Associated Tyrosine Kinase Activity, CELL 37, 1035 (1984).

Botstein et al., Construction of a Genetic Linkage Map in Man Using Restriction Fragment Length Polymorphisms, Am. J. Hum. Genet 32, 314–331 (1980).

White et al., Chromosome Mapping with DNA Markers, Scientific American 258, 40–48 (1988).

Howell et al., A Heteroplasmic I–HON Family: Tissue Distribution and Transmission of the 11778 Mutation, Am. J. Hum. Genet 55, 203–206 (1994).

Studencki et al., Discrimination among the Human $\beta^A$, $\beta^S$, and $\beta^C$–Globin Genes Using Allele–Specific Oligonucleotide Hybridization Probes, Am. J. Hum. Genet. 37, 42–51 (1985).

Saiki et al., Analysis of Enzymatically Amplified β–glogin and HLA–DQα DNA with Allele–Specific Oligonucleotide Probes, NATURE 324, 163–166 (1986).

Landegren et al., A Ligase–Mediated Gene Detection Technique, SCIENCE 241, 1077–1080 (1988).

Wu et al., Allelle–Specific Enzymatic Amplification of β–globin Genomic DNA for Diagnosis of Sickle Cell Anemia, Proc. Natl., Acad. Sci. 86, 2757–2760 (1989).

Okayama et al., Rapid Nonradioactive Detection of Mutations in the Human Genome by Allele–Specific Amplification, J. Lab. Clin. Med. 114, 105–113 (1989).

Kuppuswamy et al., Single Nucleotide Primer Extension to Detect Genetic Diseases: Experimental Application to Hemophilia B (factor IX) and Cystic Fibrosis Genes, Proc. Natl. Acad. Sci. 88, 1143–1147 (1991).

Collins et al., Rearrangement and Amplification of c–abl Sequences in the Human Chronic Myclogenous Leukemia Cell Line K–562, S.J. Proc. Natl. Acad. Sci. USA 80, 4813–4817 (1983).

Orita et al., Detection of Polymorphisms of Human DNA by Gel Electrophoresis as Single–strand Conformation Polymorphisms, Proc. Natl. Acad. Sci. USA, 86, 2766–2770 (1989).

Braun, A., et al. (1997) Improved analysis of microsatellites using mass spectrometry. Genomics, Academic Press, San Diego, US; vol. 46, pp. 18–23.

Kornher, et al. (1989) Mutation detection using nucleotide analogs that alter electrophoretic mobility, Nucleic Acids Research, Oxford University Press, vol. 17, No. 19, pp. 7779–7784.

Müeller, Sabine et al. (Mar. 2000) Retention in imprinting of the human apoptosis–related gene TSSC3 in human brain tumors. Human Molecular Genetics; vol. 9, No. 5, pp. 757–763.

European Search Report dated Dec. 1, 2003 for EP 01 30 4958.

European Search Report dated Feb. 4, 2004 for EP 01 30 4958.

Taiwanese Office Action dated Apr. 30, 2004 for Application 090113563, with English translation.

Piggee, CA, et al. (1997) Capillary electrophoresis for the detection of known point mutations by single–nucleotide primer extension and laser–induced fluorescence detection. J. Chromotography A, 781, pp. 367–375.

Kornher et al., Mutation Detection Using Nucleotide Analogs that Alter Electrophoretic Mobility, Nucleic Acids Research Oxford University Press 17:19, 7779–7784 (1989).

* cited by examiner

Fig. 1

Target DNA Detection and Quantification (1) Extension with dTTP, dGTP, dCTP, either with ddATP or without dATP (SEQ ID NO:2)
5' TGATCAGCAGGCTGAAATCGTCGTGGATTGCAACGACGCCGACGATTCTCGTCCTTTAAGGGGATAGCAT 3'
    3' gtcgtccg —————— 5'    3' cgttgctgcggctgct —————— 5'
         Primer 2        (SEQ ID NO:3)    Primer 1

(2) Extension with dATP, dGTP, dCTP, either with ddTTP or without dTTP

5' TGATCAGCAGTGCTGAAATCGTCGTGGATTGCAACGACGCCGACGATTCTCGTCCTTTAAGGGGATAGCAT 3'
    3' agcagcacc —————— 5'    3' aagagcaggaaa —————— 5'
         Primer 4        (SEQ ID NO:4)    Primer 3

(3) Extension with dATP, dGTP, dTTP, either with ddCTP or without dCTP

5' TGATCAGCAGTGCTGAAATCGTCGTGGATTGCAACGACGCCGACGATTCTCGTCCTTTAAGGGATAGCAT 3'
    3' tttag —————— 5'        3' agtaatt —————— 5'
       Primer 6                  Primer 5

Line represents primer sequence. Small letters a, g, c, and t are bases extended from the primer, some of which are labeled with a detectable marker. u and t are used interchangeably.

Fig. 2

Target RNA Detection and Quantification

(1) Extension with dTTP, dGTP, dCTP, either with ddATP or without dATP (SEQ ID NO:5)

5' UGAUCAGCAGGCUGAAAUCGUCGUGGAUUGCAACGACGCCGACGAUUCUCGUCCUUUAAGGCGAUAGCAU 3'
            3' gtcgtccg ─── 5'    3' cgttgctgcgggctgct ─── 5'
              Primer 2                  Primer 1

(2) Extension with dATP, dGTP, dCTP, either with ddTTP or without dTTP

5' UGAUCAGCAGUGCAGUGCUGAAAUCGUCGUGGAUUGCAACGAGCGCCGACGAUUCUCGUCCUUUAAGGCGAUAGCAU 3'
    3' agcagcacc ─── 5'                              3' aagagcaggaaa ─── 5'
        Primer 4                                        Primer 3

(3) Extension with dTTP, dGTP, dATP, either with ddCTP or without dCTP

5' UGAUCAGCAGUGCAGUGCUGAAAUCGUCGUGGAUUGCAACGACGCCCGACGAUUCUCGUCCUUUAAGGCGAUAGCAU 3'
    3' tttag ─── 5'                                  3' agtaatt ─── 5'
       Primer 6                                        Primer 5

Line represents primer sequence. Small letters a, g, c, and t are bases extended from the primer, some of which are labeled with a detectable marker. u and t are used interchangeably.

ISOMETRIC PRIMER EXTENSION METHOD AND KIT FOR DETECTION AND QUANTIFICATION OF SPECIFIC NUCLEIC ACID

RELATED APPLICATIONS

This application claims priority from U.S. Provisional Application Ser. No. 60/166,898, filed Nov. 22, 1999, incorporated herein by reference.

This application claims the benefit of priority date of U.S. Provisional Application No. 60/209,987, filed Jun. 8, 2000, the content of which is incorporated into the present application in its entirety.

BACKGROUND OF THE INVENTION

The present invention is related to a method for detecting and quantifying specific DNA or RNA by using an isometric primer extension (iPE) method.

Conventional methods for detecting and quantifying special sequences of nucleic acids such as DNA and RNA include southern blotting, northern analysis, and RNase protection assays, and Polymerase Chain Reaction (PCR), among other methods. However, if the detection of a specific RNA species in a sample is considered, Northern blotting and RNase protection assay present limitations in efficiency, labor intensiveness, accuracy, high cost, sensitivity, greater RNA sample requirement, specialized equipment, and a large amount of biohazardous and radioisotopic waste material that are generated. In particular, both Northern blotting and RNase protection assay require 2–3 days for completion of the analyses. In addition, Northern blotting requires running a RNA gel, transferring the RNA to a solid support, preparing a probe, and carrying out a hybridization reaction. The sensitivity requirement is a 5 $\mu$g sample for adequate sensitivity. Northern blot is based on the principle of hybridization between the target and the probe nucleic acid. Moreover, the cost per reaction is fairly high, as is the amount of biohazardous and radioisotopic waste material that are generated.

Similarly, RNase protection assay requires 2–3 days to obtain the appropriate results. The experimental procedure requires preparing template DNA, preparing RNA probe, carrying out hybridization reaction, enzyme digestion reaction, and running a gel. In order to obtain good results, a 1 $\mu$g sample of the target RNA is required. The principle behind RNase protection assay is a combination of hybridization and enzyme digestion reactions. As in the Northern blotting method, it is expensive to carry out this reaction. Furthermore, biohazardous and radioisotopic waste products are generated in high amounts. A chart comparing the various factors associated with Northern blotting, RNase protection assay and the multiple primer extension method of the present invention is set forth in Table 1.

U.S. Pat. No. 5,846,710 discloses using a primer extension technique to screen for variant DNA molecules. However, this patent does not disclose detecting a target DNA or RNA in a sample.

U.S. Pat. No. 5,994,079 discloses forming an RNA/DNA hybrid by annealing a DNA primer to a specific RNA and extending the primer by using reverse transcriptase. The hybrid is detected by an antibody specific for the RNA/DNA hybrid. However, this patent does not disclose detecting a target DNA or RNA in a sample as in the present invention.

It is recognized that there is a need in the art for a nucleic acid detection method that is simple, costs less time, is sensitive, cost effective and has a low adverse environmental impact. The present invention as described hereinbelow meets all of these needs.

SUMMARY OF THE INVENTION

The present invention has met the hereinbefore described need.

The present invention is directed to a method for detecting or quantifying a target nucleic acid in a sample comprising:
  (a) preparing a primer or primers specifically matched to a predetermined position of the target nucleic acid;
  (b) annealing the primer or primers from (a) with the target nucleic acid under high stringency conditions to obtain a primer-nucleic acid duplex at the predetermined position of the target nucleic acid;
  (c) mixing the primer-nucleic acid duplex from (b) with a mixture comprising:
    (1) one or two or three types of free non-terminator nucleotides and at least one type of non-terminator nucleotide that is optionally labeled with a detectable marker, and
    (2) with or without a type of terminator nucleotide that is different from the one or two or three types of non-terminator nucleotides in (1);
  (d) performing the primer extension by enzymatic or chemical reaction in an appropriate buffer; and either
  (e) detecting or quantifying the amount of labeling signal on the primer extended nucleotides, or
  (f) detecting or quantifying the amount of extended primers by mass spectrometry.

In the above method, the primer can be a nucleic acid primer, an oligodeoxyribonucleotide, an oligoribonucleotide, or a copolymer of deoxyribonucleic acid and ribonucleic acid. The nucleic acid of interest can be a deoxyribonucleic acid, a ribonucleic acid, or a copolymer of deoxyribonucleic acid and ribonucleic acid.

In a preferred embodiment, the method may comprise using a mixture comprising a combination of non-terminator and terminator nucleotides as follows:
  (a) dATP, dCTP, dGTP, ddTTP or ddUTP,
  (b) dATP, dCTP, dTTP or dUTP, ddGTP,
  (c) dATP, dGTP, dTTP or dUTP, ddCTP,
  (d) dCTP, dGTP, dTTP, or dUTP, ddATP,
  (e) dATP, dCTP, dGTP,
  (f) dATP, dCTP, dTTP or dUTP,
  (g) dATP, dGTP, dTTP or dUTP, or
  (h) dCTP, dGTP, dTTP or dUTP.

The method of the invention may use at least one non-terminator nucleotide that is labeled with a detectable marker. The detectable marker may comprise an enzyme or protein moiety, radioactive isotope, a fluorescent moiety, or a chemical group such as biotin. Moreover, the detecting or quantifying method step may be carried out by mass spectrometry.

Some of the enzymes used in the primer extension reaction of the invention include a template-dependent enzyme such as *E. coli* DNA polymerase I or the "Klenow fragment" thereof, T4 DNA polymerase, T7 DNA polymerase, *T. aquaticus* DNA polymerase, a retroviral reverse transcriptase, or a combination thereof.

These and other objects of the invention will be more fully understood from the following description of the invention, the referenced drawings attached hereto and the claims appended hereto.

DETAILED DESCRIPTION OF THE INVENTION

Figure 1:
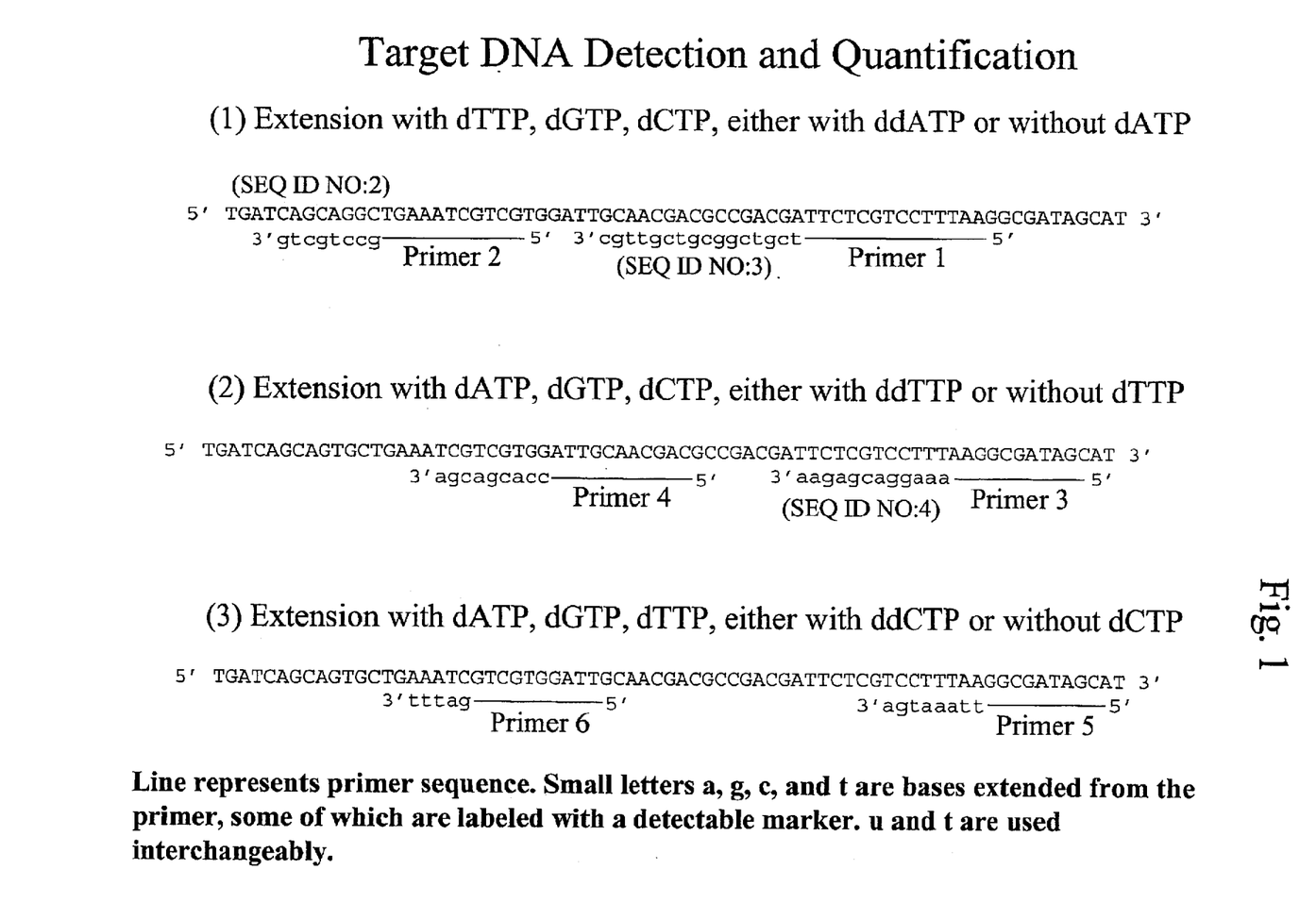
FIG. 1—a schematic of multiple primer extension reaction to detect and quantify a specific DNA sequence.
Figure 2:
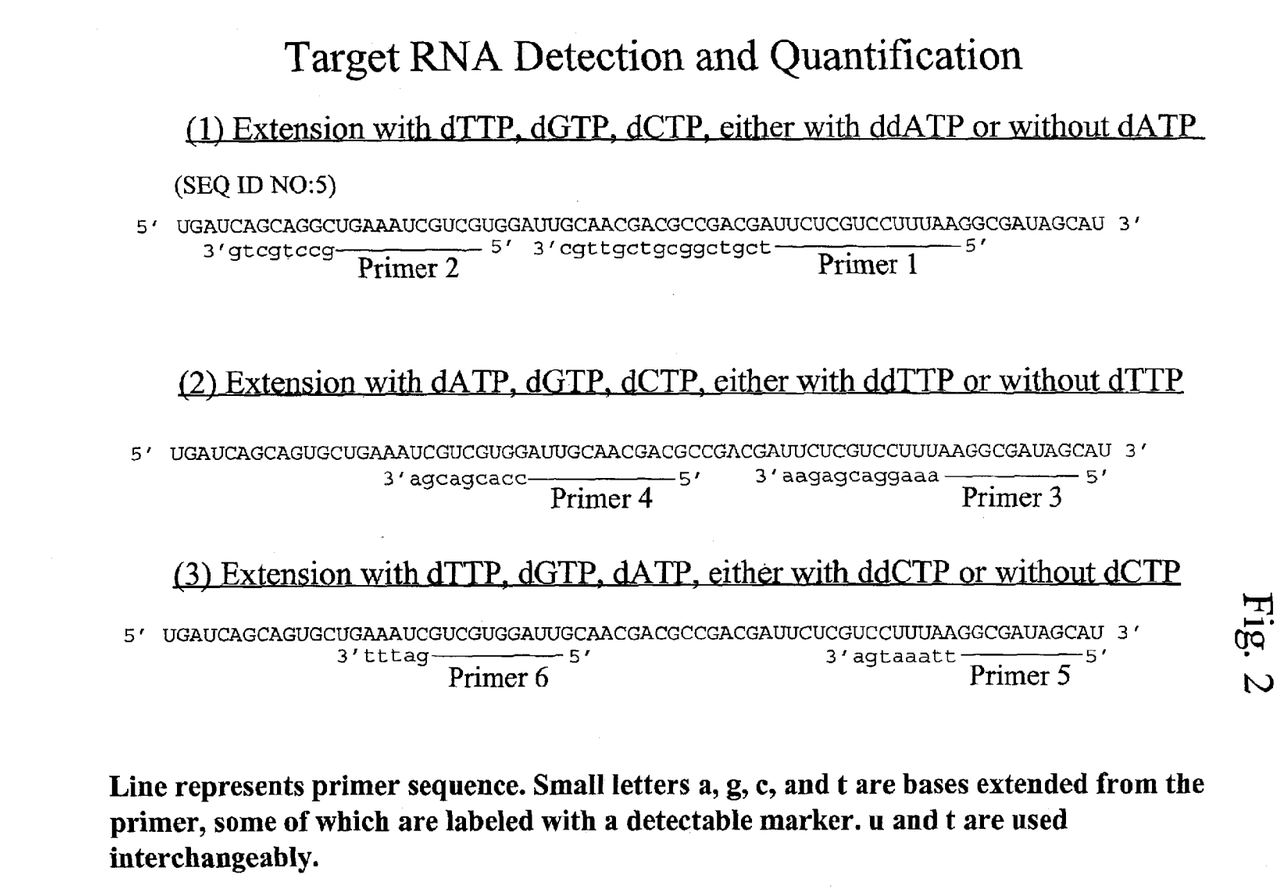
FIG. 2—a schematic for using the multiple primer extension method to detect and quantify RNA.

The present invention is directed to a method for detecting and quantifying a specific nucleotide sequence by using an isometric primer extension (iPE) method. To summarize the invention, the target DNA or RNA in the sample is hybridized to a single or multiple oligonucleotide primer. The primer(s) is then extended by DNA polymerase or reverse transcriptase in the presence of one, two or three types of the pre-labeled free nucleotide. At least one of the four required types of nucleotides for continuous extension is left out of the reaction or is replaced by the corresponding type of terminator nucleotide such as dideoxynucleotides. The specific target nucleic acid can then be detected and quantified by measuring the presence or absence of the signal generated by the label on the extended primer(s). As the extended primer is separated away from the free nucleotides, the extended primer is assayed for incorporation of the label.

The primer corresponding to a position on the target nucleic acid will be extended, and a population of equal length (isometric) primer extended nucleic acid will be made, because a definite number of nucleotides is sequence-dependently incorporated. Quantification of these equally extended primers will accurately quantify the number or amount of the target nucleic acid. If there are many copies of the target DNA or RNA in the sample, the number of copies of the primer extended product incorporating the labeled nucleotide will be correspondingly increased, contributing to a stronger overall signal. Thus, by comparing the strength of the signal observed in the unknown sample with a standardized known amount of DNA or RNA, it is possible to detect and/or quantify the amount of the target DNA or RNA in the sample. In another embodiment, the specific target nucleic acid can be detected or quantified by measuring the amount of these equal length primer extended nucleic acid species using mass spectrometry method.

The lack of a free nucleotide in the reaction buffer causes the primer extension to terminate where the missing nucleotide would have been inserted. Thus, a discrete length of the primer extension product is obtained.

Many obvious variants are possible within the realm of the present invention. For example, not just one type of nucleotide but two or three types of nucleotides maybe absent in the primer extension reaction. Also, various labels could be used, which are not limited to radioactive nucleotides but can be fluorescent, as well as enzymatic.

As used herein, "nucleic acid" or "nucleotide" can be a deoxyribonucleic acid, a ribonucleic acid, or a copolymer of deoxyribonucleic acid and ribonucleic acid. The sample of nucleic acids can be natural or synthetic. The sample of nucleic acid can be naturally occurring nucleic acid, and can be obtained from any organism. Some examples of organisms to which the method of the present invention is applicable include plants, microorganisms, viruses, birds, vertebrates, invertebrates, mammals, human beings, horses, dogs, cows, cats, pigs, or sheep. The target nucleic acid can occur naturally, or can be synthesized enzymatically in vivo, synthesized enzymatically in vitro, or synthesized non-enzymatically.

The sample containing the nucleic acid or acids of interest can comprise genomic DNA from an organism, RNA transcripts thereof, or cDNA prepared from RNA transcripts thereof. The sample containing the nucleic acid or acids of interest can also comprise extragenomic DNA from an organism, RNA transcripts thereof, or cDNA prepared from RNA transcripts thereof. Also, the nucleic acid or acids of interest can be synthesized by the polymerase chain reaction.

The nucleic acid of interest can comprise non-natural nucleotide analogs such as deoxyinosine or 7-deaza-2-deoxyguanosine. These analogues destabilize DNA duplexes and could allow a primer annealing and extension reaction to occur in a double-stranded sample without completely separating the strands.

The nucleic acid of interest can comprise one or more moieties that permit affinity separation of the nucleic acid of interest from the unincorporated reagent and/or the primer. For example, the nucleic acid of interest can comprise biotin which permits affinity separation of the nucleic acid of interest from the unincorporated reagent and/or the primer via binding of the biotin to the avidin family of molecules, which is attached to a solid support. The sequence of the nucleic acid of interest can comprise a DNA or RNA sequence that permits affinity separation of the nucleic acid of interest from the unincorporated reagent and/or the primer via base pairing to a complementary sequence present in a nucleic acid attached to a solid support. The nucleic acid of interest can be labeled with a detectable marker; this detectable marker can be different from any detectable marker present in the reagent or attached to the primer.

In this regard, the term "normal nucleotide" or "normal base" is defined as the wild-type or previously known standard nucleotide base from which a mutation is sought to be identified at the base site. By "standard nucleotide base", it includes any known base, which may include wild-type or a known mutant base so long as the base is known and it is desired to know its variant. Thus, as an example, normal base can be a known wild-type base for which a mutation is sought at the position. Reversely, the known base can be a known mutant for which the presence of a wild-type base is sought at the position. Alternatively, the known normal base can be a known mutant for which another mutant variant base is sought. Therefore, the method of the invention can be applied to any known sequence that can be used to determine the presence of any other base variant at the site.

As used herein, the term "primer" or "oligonucleotide primer" refers to an oligonucleotide which is capable of acting as a point of initiation of synthesis when placed under conditions that allow for synthesis of a primer extension product which is complementary to a nucleic acid (template) strand, in the presence of various factors such as for example, nucleotides and enzymes such as DNA polymerase, and at a suitable temperature and pH.

The term "primer" is alternatively defined as any nucleic acid fragment obtained from any source. For example, the primer can be produced by fragmenting larger nucleic acid fragments such as genomic DNA, cDNA or DNA that has been obtained through PCR. In other words, the nature of the primer is not limited by how the primer is obtained, whether it be by fragmenting naturally or synthetically occurring nucleic acid or by synthesizing the nucleic acid primer. Furthermore, the primer can be oligodeoxyribonucleotide, a copolymer of oligodeoxyribonucleotides, an oligoribonucleotides, a copolymer of ribonucleotides, or a copolymer of deoxyribonucleotides and ribonucleotides. The primer can be either natural or synthetic. The oligonucleotide primer can be synthesized either enzymatically in vivo, enzymatically in vitro, or non-enzymatically in vitro. The primer can be labeled with a detectable marker; this detectable marker can be different from any detectable marker present in the reagent or attached to the nucleic acid of interest. In addition, the primer must possess sequence corresponding to the flanking sequence at a specific position of interest adjacent to, and upstream of, the nucleotide base to be identified.

In addition, the primer must be capable of hybridizing or annealing with nucleotides present in the nucleic acid of interest. One way to accomplish the desired hybridization is to have the template-dependent primer be substantially complementary or fully complementary to the known base sequence.

The oligonucleotide primer can comprise one or more moieties that link the primer to a solid support for affinity separation of the primer from the unincorporated reagent and/or the nucleic acid of interest. Such affinity moeties include, but are not limited to, digitonin, magnetic beads, and ligands, such as protein ligands, including antibodies. Preferably, the moiety is biotin. In the case of using biotin, the primer comprising biotin permits affinity separation of the primer from the unincorporated reagent and/or nucleic acid of interest via binding of the biotin to streptavidin which is attached to a solid support. The sequence of the oligonucleotide primer can comprise a DNA sequence that permits affinity separation of the primer from the unincorporated reagent and/or the nucleic acid of interest via base pairing to a complementary sequence present in a nucleic acid attached to a solid support.

As used herein, the term "primer extension reaction" refers to the reaction conditions in which the template-dependent nucleic acid synthesis reaction is carried out. The conditions for the occurence of the template-dependent, primer extension reaction can be created, in part, by the presence of a suitable template-dependent enzyme. Some of the suitable template-dependent enzymes are DNA polymerases. The DNA polymerase can be of several types. The DNA polymerase must, however, be primer and template dependent. For example, E. coli DNA polymerase I or the "Klenow fragment" thereof, T4 DNA polymerase, T7 DNA polymerase ("Sequenase"), T. aquaticus DNA polymerase, or a retroviral reverse transcriptase can be used. RNA polymerases such as T3 or T7 RNA polymerase could also be used in some protocols. Depending upon the polymerase, different conditions must be used, and different temperature ranges may be required for the hybridization and extension reactions.

As used herein, the term "primer extension strand" includes the strand that is formed opposite the template in a duplex after the primer has been added. Preferably, the extension of the primer is terminated by the incorporation of the terminator to the primer extension strand.

As used herein, the term "template" is defined as a nucleic acid, including double strand DNA, single strand DNA and RNA, or any modification thereof, and can be any length or sequence.

As used herein, the term "terminator" or "chain terminator" is meant to refer to a nucleic acid base, such as A, G, C, T or U, or an analogue that effectively terminates the primer extension reaction when it is incorporated into the primer extension strand opposite the template strand. Preferably, the terminator is a dideoxynucleotide. Also preferably, the terminator is either unlabeled or is labeled so that it is distinguished from the label on the non-terminator.

Also as used herein, when the term "terminator" or "chain terminator" are referred to in the singular, it does not mean that a single nucleotide molecule is used. Rather, the singular form of the term "terminator" refers to the type of nucleotide, nucleic acid base or nucleic acid analogue that is used in the assay. For example, if the terminator is ddA, then all of the ddA's in the aggregate are referred to in the singular form, and not just a single molecule of ddA. Alternatively, the "terminator" may be the absence of the specific type of nucleotide so that primer extension is stopped by the lack of the specific nucleotide at the locus. For example, if it is desired that the primer extension reaction be stopped opposite a "C" on the template strand, the non-terminating bases A, T and G should be included in the primer extension reaction mixture, but not "G", which is the complement of "C". Thus, the absence of the complementary base will cause termination of the primer extension reaction with a similar result as adding a dideoxy terminator nucleotide, for example.

As used herein, the term "non-terminator" or "non-chain terminator" includes a nucleotide base that does not terminate the extension reaction when it is incorporated into the primer extension strand. Preferably, at least one non-terminator in the primer extension reaction is labeled. Also as used herein, when the term "non-terminator" or "non-chain terminator" are referred to in the singular, it does not mean that a single nucleotide molecule is used. Rather, the singular form of the term "non-terminator" refers to the type of nucleotide, nucleic acid base or nucleic acid analogue that is used in the assay. For example, if the terminator is G, then all of the G's in the aggregate are referred to in the singular form, and not just a single molecule of G.

As used herein, the term "mutant" or "mutation" indicates any base on the template strand that is different from the wild-type or normal base. The mutation that can be detected using the method of the instant invention can be any type of mutation at all, including, single base mutation, insertion, deletion, or gene translocation, so long as the base on the template directly opposite to the base immediately 3' to the annealed primer is affected.

As used herein, the term "label" refers to any molecule that is linked to the terminator or non-terminator nucleotide to provide a detectable signal. The label may be radioactive, chemiluminescent, protein ligand such as an antibody, or if a fluorescent group is used, a different fluorescent group may be used for each type of non-terminating nucleotide base. These fluorescent tags would have the property of having spectroscopically distinguishable emission spectra.

Alternatively, the method of determining the level of incorporation of a nucleotide base in the primer extension product can be measured by mass spectrometry techniques as exemplified in U.S. Pat. No. 5,885,775, which is incorporated herein by reference in its entirety.

As used herein, the phrase "high stringency hybridization conditions" refers to nucleic hybridization conditions, such as but not limited to a wash condition of 0.1×SSC, at 42° C. Hybridization conditions generally can be found in general Molecular Biology protocol books, such as Ausubel et al., Current Protocols in Molecular Biology Greene and Wiley, pub. (1994), which is incorporated herein by reference in its entirety.

As used herein, "thin layer chromatography (TLC)" can be carried out in paper medium based on cellulose products, but can be made of any substance that allows for molecules to be finely divided and formed into a uniform layer. This substance includes, but is not limited to, inorganic substances such as silica gel, aluminum oxide, diatomaceous earth or magnesium silicate. Organic substances include, but are not limited to, cellulose, polyamide, or polyethylene powder. Thin layer chromatography methods are described generally in Chemical protocol books, such as generally set forth in Freifelder, *Physical Biochemistry—Applications to Biochemistry and Molecular Biology, second ed.*, published by Freeman and Co. (1982), which is incorporated herein by reference in its entirety, especially Chapter 8, which discusses chromatographic techniques, and in particular thin layer chromatography at pages 229–232.

A modification of the method for indentifying and/or quantifying a nucleic acid of interest is to separate the primer extended strand from the nucleic acid of interest after the extension reaction by using appropriate denaturing conditions. The denaturing conditions can comprise heat, alkali, formamide, urea, glyoxal, enzymes, and combinations thereof. The denaturing conditions can also comprise treatment with 2.0N NaOH.

It can be appreciated by a person of skill in the art that the terminator can be labeled with a different label from the non-terminator, which can then be used to differentiate between incorporation of terminator or non-terminator in the primer extension strand. The terminator exemplified as being the absence of the particular type of nucleotide in the present application only for purposes of simplicity of illustration, but this illustration should not be construed to limit the claims in any way. Differentially labeled or unlabeled terminator is also encompassed by the invention, so long as the label on the terminator is different from the label on the non-terminator.

It can also be appreciated by a person of skill in the art that so long as the sequence of the template is at least partially known, a primer can be designed that binds to the template strand such that the binding of the primer on the template strand can occur. It can also be appreciated by a person of skill in the art that the method of the invention can be practiced by using several primers in one or more assay tube.

A feature of the method of the invention is that strong signal can be generated if the non-terminators are uniformly labeled because of the additive signal effect achieved by the incorporation of several labeled non-terminators incorporated in the primer extension strand. Accuracy is enhanced when signals are observed from using different labels specific to various terminators or non-terminators.

It is also an object of this invention to provide a kit and reagents for rapidly and accurately determining the presence or absence of a target nucleic acid in a sample quantitatively or non-quantitatively as desired. Each component of the kit(s) may be individually packaged in its own suitable container. The individual containers may also be labelled in a manner which identifies the contents. Moreover, the individually packaged components may be placed in a larger container capable of holding all desired components. Associated with the kit may be instructions which explain how to use the kit. These instructions may be written on or attached to the kit.

The following examples are offered by way of illustration of the present invention, and not by way of limitation.

EXAMPLE

Total RNA was extracted from rat brain by RNAzol B (Tels-tel, TX) method. The concentration of total RNA was measured by O.D. 260 nm absorbance. Total RNA was diluted by RNase-free diethylpyrocarbonate (DEPC) treated water. 5 $\mu$l of diluted RNA solution with different amounts as indicated in Table 2 was aliquoted into each tube and then mixed with 1 $\mu$l synthetic oligonucleotide primer 5'-GTGGGAACCGTGTCA-3' (SEQ ID NO:1), which is a sequence matched to a rat brain specific cDNA (unpublished data). The RNA-primer mixture was heated at 70° C. for 3 minutes and incubated on ice for 3 minutes. After quick spinning the tube, the primer extension reaction was started by adding 14 $\mu$l reaction mix containing Tris-HCl buffer (pH 7.5) at final concentration of 20 mM, 15 units RNase inhibitor, 0.5 mM dATP, dGTP, 1 $\mu$l dCTP$\alpha^{32}$P and 10 units MMVL-reverse transcriptase. The reaction was performed at 37° C. for 20 minutes and stopped by heating the reaction tube at 100° C. for 2 minutes. A 1 $\mu$l reaction mixture was applied to a thin layer chromatography (TRIM USA, Maryland) to separate out free dCTP$\alpha^{32}$P. The radioactivity of the labeled primer was then subjected to counting by scintillation counter (Beckman LS 5000). The results are shown in Table 2.

All of the above steps involve chemistries, manipulations, and protocols that have been, or are amenable to being, automated. Thereby, incorporation of the preferred mode of practice of this invention into the operation of a suitably programmed robotic workstation should result in significant cost savings and increases in productivity for virtually any diagnostic procedure that depends on the detection of specific nucleotide sequences or sequence differences in nucleic acids derived from biological samples.

All of the references cited herein are incorporated by reference in their entirety.

TABLE 1

Comparison of MPE method with Northern analysis and RNase protection assay

| Methods | Time consuming | Experiment procedure | Sensitivity | Principle | Expense | Biohazard/ Radioisotope wastes |
|---|---|---|---|---|---|---|
| Northern analysis | 2–3 days | Running RNA gel RNA Transfer Prepare probe Hybridization | 5 $\mu$g | Hybridization only | High | High |
| RNase Protection Assay | 2–3 days | Prepare template DNA Prepare RNA probe Hybridization Enzyme digestion Running gel | 1 $\mu$g | Hybridization and enzyme digestion | High | High |
| MPE | 1 hour | Primer extension | 1 ng | Hybridization and specific extension | Low | Low |

TABLE 2

| RNA amount (ng) | Labeled primer (cpm) |
|---|---|
| 20 | 31552 |
| 10 | 29756 |
| 5 | 26066 |
| 2 | 16779 |
| 1 | 11156 |
| 0.5 | 6587 |
| 0 | 6703 |

What is claimed is:

1. A method for detecting or quantifying a target nucleic acid in a sample comprising:
   (a) preparing at least one primer specifically matched to a predetermined position of the target nucleic acid;
   (b) annealing the at least one primer from (a) with the target nucleic acid to obtain a primer-nucleic acid duplex at the predetermined position of the target nucleic acid;
   (c) mixing the primer-nucleic acid duplex from (b) with a non-terminator nucleotide mixture consisting of:
      (i) dATP, dCTP, dGTP;
      (ii) dATP, dCTP, dTTP or dUTP;
      (iii) dATP, dGTP, dTTP or dUTP; or
      (iv) dCTP, dGTP, dTTP or dUTP
   wherein at least one non-terminator nucleotide of the non-terminator nucleotide mixture is labeled with a detectable marker;
   (d) performing isometric primer extension by enzymatic or chemical reaction in an appropriate buffer to form isometric primer extension products, wherein the primer extension terminates at a target nucleic acid nucleotide complementary to an omitted non-terminator nucleotide of (c); and
   (e) detecting or quantifying the amount of labeling signal on the isometric primer extension products.

2. The method according to claim 1, wherein the at least one primer is selected from the group consisting of a nucleic acid primer, an oligodeoxyribonucleotide, an oligoribonucleotide, and a copolymer of deoxyribonucleic acid and ribonucleic acid.

3. The method according to claim 1, wherein the target nucleic acid is selected from the group consisting of a deoxyribonucleic acid, a ribonucleic acid, and a copolymer of deoxyribonucleic acid and ribonucleic acid.

4. The method according to claim 1, wherein the non-terminator nucleotides are selected from the group consisting of deoxyribonucleotides and ribonucleotides.

5. The method according to claim 1, wherein said detectable marker is selected from the group consisting of an enzyme moiety, protein moiety, radioactive isotope, fluorescent moiety, and a chemical group.

6. The method according to claim 1, wherein the primer extension products are formed using a template-dependent enzyme.

7. The method according to claim 6, wherein the template-dependant enzyme is selected from the group consisting of DNA polymerase, RNA polymerase, and reverse transcriptase.

8. The method according to claim 6, wherein the template-dependant enzyme is *E. coli* DNA polymerase I, a Klenow fragment thereof, T4 DNA polymerase, T7 DNA polymerase, Thermophilic DNA polymerase, retroviral reverse transcriptase, or a combination thereof.

9. The method according to claim 1, wherein the target nucleic acid is synthesized enzymatically in vivo, or in vitro.

10. The method according to claim 1, wherein the target nucleic acid is synthesized by polymerase chain reaction.

11. The method according to claim 1, wherein the target nucleic acid comprises non-natural nucleotide analogs.

12. The method according to claim 11, wherein the non-natural nucleotide analogs comprise deoxyinosine or 7-deaza-2'-deoxyguanosine.

13. The method according to claim 1, wherein the target nucleic acid is selected from the group consisting of genomic DNA from an organism, RNA transcripts thereof, and cDNA prepared from RNA transcripts thereof.

14. The method according to claim 13, wherein the organism is a plant, microorganism, bacteria, or virus.

15. The method according to claim 13, wherein the organism is a vertebrate or invertebrate.

16. The method according to claim 13, wherein the organism is a mammal.

17. The method according to claim 16, wherein the mammal is a human being.

18. The method according to claim 1, wherein an amplification step is performed on the target nucleic acid.

19. The method according to claim 18, wherein the amplification step comprises an amplification method selected from the group consisting of cloning, transcription, polymerase chain reaction (PCR), ligase chain reaction (LCR), strand displacement amplification (SDA), and loop mediated isothermal amplification (LAMP).

20. The method according to claim 1, wherein the primer comprises at least one moiety that permits affinity separation of the primer from the unincorporated reagent or the nucleic acid of interest.

21. The method according to claim 1, wherein the primer comprises at least one moiety that allows immobilization of the primer onto a solid support to produce an immobilized primer sequence.

22. The method according to claim 20 or 21, wherein the at least one moiety comprises a special chemical group selected from the group consisting of biotin, and digitonin.

23. The method according to claim 20 or 21, wherein the at least one moiety comprises a nucleotide sequence that allows the primer to link to a solid support, the solid support having a complementary sequence to the nucleotide sequence of the at least one moiety, wherein the primer links to the solid support via base pairing to the complementary sequence present in the solid support.

24. The method according to claim 1, wherein the primer is directly synthesized on a solid support to produce an immobilized primer sequence.

25. The method according to claim 24, wherein the synthesis is accomplished by enzymatic or chemical or physical method.

26. The method according to claim 1, wherein the primer is immobilized onto a solid support to produce immobilized isometric primer extension products.

27. The method according to claim 1, wherein the primer is reversibly immobilized onto a solid support.

28. The method according to claim 27, wherein the primer is cleaved from the solid support by a chemical, enzymatic or physical process.

29. The method according to claim 1, wherein the target nucleic acid is immobilized onto a solid support to produce immobilized isometric primer extension products.

30. The method according to claim 1, wherein the target nucleic acid is reversibly immobilized onto a solid support.

31. The method according to claim 29, wherein the target nucleic acid is cleaved from the solid support by a chemical, enzymatic or physical process.

32. The method according to claim 26, 27, 29 or 30, wherein immobilization is accomplished via a photocleavable bond.

33. The method according to claim 21, 24, 26, 27, 29 or 30, wherein the solid support is selected from the group consisting of beads, flat surfaces, chips, capillaries, pins, and wafers.

34. The method according to claim 26, 27, 29, or 30, wherein said immobilization is accomplished by hybridization between a complimentary capture nucleic acid molecule, which has been previously immobilized to a solid support, and a portion of the nucleic acid molecule, which is distinct from the target nucleic acid sequence.

35. The method according to claim 26, 27, 29, or 30, wherein said immobilization is accomplished via direct bonding between the solid support and a portion of the nucleic acid molecule, which is distinct from the target nucleic acid sequence.

36. A method to detect or quantify at least one nucleic acid in a sample, the method comprising the steps of:
   (a) annealing a primer to a target nucleic acid;
   (b) extending the primer to form isometric primer extension products using a non-terminator nucleotide mixture consisting of:
      (i) dATP, dCTP, dGTP;
      (ii) dATP, dCTP, dTTP or dUTP;
      (iii) dATP, dGTP, dTTP or dUTP; or
      (iv) dCTP, dGTP, dTTP or dUTP
   wherein at least one nucleotide is fluorescently labeled; and
   (c) assaying for incorporation of the fluorescently labeled nucleotide within the isometric extension products.

37. The method according to claim 1, wherein the target nucleic acid is synthesized non-enzymatically.

38. The method according to claim 23, wherein the solid support is selected from the group consisting of beads, flat surfaces, chips, capillaries, pins, and wafers.

* * * * *

UNITED STATES PATENT AND TRADEMARK OFFICE
CERTIFICATE OF CORRECTION

PATENT NO. : 6,824,980 B2
DATED : November 30, 2004
INVENTOR(S) : Wang

It is certified that error appears in the above-identified patent and that said Letters Patent is hereby corrected as shown below:

Title page,
Item [60], Related U.S. Application Priority Data, delete "and provisional application No. 60/166,898, filed on Nov. 22, 1999"
Item [56], References Cited, OTHER PUBLICATIONS,
"Howell" reference, delete "I-HON" and insert -- LHON --;
"Collins" reference, delete "Myclogenous" and insert -- Myelogenous --;
"Piggee" reference, delete "Chromotography" and insert -- Chromatography --.
Add the following references:
-- Fahy et al. Multiplex Fluorescence-based Primer Extension Method for Quantitative Mutation Analysis of Mitochondrial DNA and its Diagnostic Application for Alzheimer's Disease, NUCLEIC ACID RESEARCH 25, 3102-3109 (1997).

Kinzler et al. Identification of FAP Locus Genes from Chromosome 5q21, SCIENCE 253, 661-665 (1991)

Joslyen et al. Deletion Mutations and Three New Genes at the Familial Polyposis Locus, CELL 66, 601-613 (1991) --

Signed and Sealed this

Tenth Day of May, 2005

JON W. DUDAS
*Director of the United States Patent and Trademark Office*

SEQUENCE LISTING

<160> NUMBER OF SEQ ID NOS: 5

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 1
gtgggaaccg tgtca                                                      15

<210> SEQ ID NO 2
<211> LENGTH: 70
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 2
tgatcagcag gctgaaatcg tcgtggattg caacgacgcc gacgattctc gtcctttaag     60
gcgatagcat                                                            70

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 3
tcgtcggcgt cgttgc                                                     16

<210> SEQ ID NO 4
<211> LENGTH: 12
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 4
aaaggacgag aa                                                         12

<210> SEQ ID NO 5
<211> LENGTH: 70
<212> TYPE: RNA
<213> ORGANISM: Artificial Sequence -continued

```
<220> FEATURE:
<223> OTHER INFORMATION: Description of Artificial Sequence: synthetic
      oligonucleotide

<400> SEQUENCE: 5
ugaucagcag gcugaaaucg ucguggauug caacgacgcc gacgauucuc guccuuuaag      60
gcgauagcau                                                             70
```